(12) United States Patent
Blake et al.

(10) Patent No.: US 11,202,444 B2
(45) Date of Patent: Dec. 21, 2021

(54) RED TRANSGENIC FLUORESCENT ORNAMENTAL FISH

(71) Applicant: GloFish, LLC, Earth City, MO (US)

(72) Inventors: Alan Blake, Austin, TX (US); Richard Crockett, Wilton, CT (US); Aidas Nasevicius, Tampa, FL (US)

(73) Assignee: GloFish, LLC, Earth City, MO (US)

( * ) Notice: Subject to any disclaimer, the term of this patent is extended or adjusted under 35 U.S.C. 154(b) by 0 days.

(21) Appl. No.: 16/160,586

(22) Filed: Oct. 15, 2018

(65) Prior Publication Data

US 2019/0110449 A1  Apr. 18, 2019

Related U.S. Application Data

(63) Continuation of application No. 15/450,338, filed on Mar. 6, 2017, now Pat. No. 10,098,334.

(51) Int. Cl.
*A01K 67/027* (2006.01)
*C07K 14/435* (2006.01)
*A01K 67/02* (2006.01)

(52) U.S. Cl.
CPC .......... *A01K 67/0275* (2013.01); *A01K 67/02* (2013.01); *C07K 14/43595* (2013.01); *A01K 2217/052* (2013.01); *A01K 2227/40* (2013.01); *A01K 2267/02* (2013.01)

(58) Field of Classification Search
CPC .................................................. A01K 67/0275
See application file for complete search history.

(56) References Cited

U.S. PATENT DOCUMENTS

| | | | |
|---|---|---|---|
| 7,135,613 B1 | 11/2006 | Gong et al. | |
| 7,700,825 B2 | 4/2010 | Blake et al. | |
| 7,834,239 B2 | 11/2010 | Gong et al. | |
| 8,153,858 B2 | 4/2012 | Gong et al. | |
| 8,232,450 B1 | 7/2012 | Blake et al. | |
| 8,232,451 B1 | 7/2012 | Blake et al. | |
| 8,378,169 B2 | 2/2013 | Gong et al. | |
| 8,581,023 B2 | 11/2013 | Blake et al. | |
| 8,581,024 B2 | 11/2013 | Blake et al. | |
| 8,581,025 B2 | 11/2013 | Blake et al. | |
| 8,975,467 B2 | 3/2015 | Blake et al. | |
| 8,987,546 B2 | 3/2015 | Blake et al. | |
| 9,271,478 B2 | 3/2016 | Blake et al. | |
| 9,282,729 B2 | 3/2016 | Blake et al. | |
| 9,295,237 B2 | 3/2016 | Blake et al. | |
| 9,295,238 B2 | 3/2016 | Blake et al. | |
| 9,363,986 B2 | 6/2016 | Blake et al. | |
| 9,380,768 B2 | 7/2016 | Blake et al. | |
| 9,392,776 B2 | 7/2016 | Blake et al. | |
| 2010/0050280 A1 | 2/2010 | Blake et al. | |
| 2010/0145889 A1 | 6/2010 | Blaket et al. | |
| 2014/0007265 A1 | 1/2014 | Gong et al. | |
| 2014/0224182 A1 | 8/2014 | Blake et al. | |
| 2016/0128310 A1 | 5/2016 | Blake et al. | |
| 2017/0006843 A1 | 1/2017 | Blake et al. | |

FOREIGN PATENT DOCUMENTS

WO  WO2008/022208  2/2008

OTHER PUBLICATIONS

Acceptance of patent deposit issued by Public Health England Poton Down and European Collection of Authenticated Cell Cultures for Tiger Barb Sperm (Barb 2016-R), deposit Reference No. 16121901, Dec. 19, 2016.
Design U.S. Appl. No. 29/501,874 entitled "Bright Red Fluorescent Tetra" by Alan Blake et al., filed Sep. 9, 2014.
Design U.S. Appl. No. 29/501,878 entitled "Bright Blue Fluorescent Tetra" by Alan Blake et al., filed Sep. 9, 2014.
Design U.S. Appl. No. 29/504,232 entitled "Green Striped Fluorescent Barb Fish" by Alan Blake et al., filed Oct. 3, 2014.
U.S. Appl. No. 13/396,492 entitled "Recombinant Constructs and Transgenic Fluorescent Ornamental Fish Therefrom" by Alan Blake et al., filed Feb. 14, 2012.

*Primary Examiner* — Valarie E Bertoglio
(74) *Attorney, Agent, or Firm* — Merchant & Gould P.C.

(57) ABSTRACT

The present invention relates to transgenic red ornamental fish, as well as methods of making such fish by in vitro fertilization techniques. Also disclosed are methods of establishing a population of such transgenic fish and methods of providing them to the ornamental fish industry for the purpose of marketing.

12 Claims, No Drawings

RED TRANSGENIC FLUORESCENT ORNAMENTAL FISH

CROSS-REFERENCE TO RELATED APPLICATIONS

This application is a continuation of U.S. application Ser. No. 15/450,338, filed Mar. 6, 2017, which claims the benefit of U.S. Provisional Application No. 62/306,703, filed Mar. 11, 2016, the disclosures of which are incorporated herein in their entirety.

BACKGROUND OF THE INVENTION

The present claims priority to U.S. Provisional Application No. 62/306,703 filed on Mar. 11, 2016, the entire contents of which are specifically incorporated herein by reference without disclaimer.

1. Field of the Invention

This invention relates to transgenic fish, particularly red transgenic fish.

2. Description of Related Art

Transgenic technology involves the transfer of a foreign gene into a host organism enabling the host to acquire a new and inheritable trait. Transgenic technology has many potential applications. For example, it can be used to introduce a transgene into a fish in order to create new varieties of fish. There are many ways of introducing a foreign gene into fish, including: microinjection (e.g., Zhu et al., 1985; Du et al., 1992), electroporation (Powers et al., 1992), sperm-mediated gene transfer (Khoo et al., 1992; Sin et al., 1993), gene bombardment or gene gun (Zelenin et al., 1991), liposome-mediated gene transfer (Szelei et al., 1994), and the direct injection of DNA into muscle tissue (Xu et al., 1999). The first transgenic fish report was published by Zhu et al., (1985) using a chimeric gene construct consisting of a mouse metallothionein gene promoter and a human growth hormone gene. Most of the early transgenic fish studies have concentrated on growth hormone gene transfer with an aim of generating fast growing fish. While a majority of early attempts used heterologous growth hormone genes and promoters and failed to produce these fish (e.g. Chourrout et al., 1986; Penman et al., 1990; Brem et al., 1988; Gross et al., 1992), enhanced growth of transgenic fish has been demonstrated in several fish species including Atlantic salmon, several species of Pacific salmons, and loach (e.g. Du et al., 1992; Delvin et al., 1994, 1995; Tsai et al., 1995).

The tiger barb (*Puntius tetrazona*, or, historically, *Barbus tetrazona*, syn. *Capoeta tetrazona*, also known commonly as the Sumatra barb), originally from Asia (more specifically, Malaysia, Indonesia, and Borneo) has been commercially cultured in the United States at least as early as 1950 (Innes, 1950). The species name "*tetrazona*" refers to the four vertical stripes seen on the wild-type tiger barb. However, for the ornamental fish industry the dark striped pigmentation of the adult tiger barb does not aid in the efficient display of various colors. The albino tiger barb, or "albino barb" is a variant that arose during domestication and shows decreased pigmentation. The availability of such fish having modified pigmentation for transgenesis with fluorescent proteins would result in better products for the ornamental fish industry due to better visualization of the various colors.

Many fluorescent proteins are known in the art and have been used to investigate various cellular processes, including fluorescent proteins exhibiting various green, red, pink, yellow, orange, blue, or purple colors. Although transgenic experiments involving fluorescent proteins have provided new markers and reporters for transgenesis, progress in the field of developing and producing ornamental fish that express such proteins has been limited.

SUMMARY OF THE INVENTION

In certain embodiments, the present invention concerns making transgenic fluorescent fish and providing such fish to the ornamental fish industry.

In some embodiments, transgenic fish or methods of making transgenic fish are provided. In certain aspects, the transgenic fish are fertile, transgenic, fluorescent fish. In a particular embodiment, the fish for use with the disclosed constructs and methods is the albino barb. Barb skin color is determined by pigment cells in their skin, which contain pigment granules called melanosomes (black or brown color), xanthosomes (yellow color), erythrosomes (orange or red color), or iridosomes (iridescent colors, including white color). The number, size, and density of the pigment granules per pigment cell influence the color of the fish skin. Albino barb have diminished number, size, and density of melanosomes and hence have lighter skin when compared to the wild type tiger barb.

In certain specific embodiments there are provided transgenic barbs or progeny thereof comprising specific transgenic integration events, referred to herein as transformation events. These fish are of particular interest because, for example, they embody an aesthetically pleasing red color. Transgenic fish comprising these specific transgenic events may be homozygous or heterozygous (including, for example, hemizygous) for the transformation event. Homozygous fish bred with fish lacking a transformation event will in nearly all cases produce 100% heterozygous offspring. Eggs, sperm, and embryos comprising these specific transgenic events are also included as part of the invention.

In one such embodiment regarding a specific transgenic integration event, a red transgenic barb or progeny thereof is provided comprising chromosomally integrated transgenes, wherein the barb comprises the "Red barb 1 transformation event," sperm comprising the Red barb 1 transformation event having been deposited as ECACC accession no. 16121901. The chromosomally integrated transgenes may be present on one integrated expression cassette or two or more integrated expression cassettes. In certain aspects, such a transgenic barb is a fertile, transgenic barb. In more specific aspects, such a barb is a transgenic albino barb. Such a transgenic barb may be homozygous or heterozygous (including, for example, hemizygous) for the transgenes or integrated expression cassette(s).

Also disclosed are methods of providing a transgenic barb comprising the Red barb 1 transformation event to the ornamental fish market. In some embodiments, the method comprises obtaining a transgenic barb comprising chromosomally integrated transgenes, wherein the barb comprises the "Red barb 1 transformation event," sperm comprising the Red barb 1 transformation event having been deposited as ECACC accession no. 16121901, and distributing the fish to the ornamental fish market. Such fish may be distributed by a grower to a commercial distributor, or such fish may be distributed by a grower or a commercial distributor to a retailer such as, for example, a multi-product retailer having an ornamental fish department.

In some aspects, methods of producing a transgenic barb are provided comprising: (a) obtaining a barb that exhibits fluorescence and comprises one or more chromosomally integrated transgenes or expression cassettes, wherein the barb comprises the "Red barb 1 transformation event," sperm comprising the Red barb 1 transformation event having been deposited as ECACC accession no. 16121901; and (b) breeding the obtained barb with a second barb to provide a transgenic barb comprising the Red barb 1 transformation event. The second barb may be a transgenic or non-transgenic barb.

In further embodiments, also provided are methods of producing a transgenic organism, the method comprising using sperm comprising the Red barb 1 transformation, such sperm having been deposited as ECACC accession no. 16121901, to produce transgenic offspring. Such offspring may be, for example, a barb, a species of the Puntius genus, a fish species or genus related to barb, or another fish species or genus. In some aspects, the fish may be produced using in vitro fertilization techniques known in the art or described herein.

As used in this specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Any embodiment of any of the present methods, kits, and compositions may consist of or consist essentially of—rather than comprise/include/contain/have—the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Transgenic Fish

In some aspects, the invention regards transgenic fish. Methods of making transgenic fish are described in, for example, U.S. Pat. Nos. 7,135,613; 7,700,825; 7,834,239, each of which is incorporated by reference in its entirety.

It is preferred that fish belonging to species and varieties of fish of commercial value, particularly commercial value within the ornamental fish industry, be used. Such fish include but are not limited to catfish, zebrafish, medaka, carp, tilapia, goldfish, tetras, barbs, sharks (family cyprinidae), angelfish, loach, koi, glassfish, catfish, discus, eel, tetra, goby, gourami, guppy, Xiphophorus, hatchet fish, Molly fish, or pangasius. A particular fish for use in the context of the invention is a barb, Puntius tetrazona. Barb are increasingly popular ornamental animals and would be of added commercial value in various colors. Barb embryos are easily accessible and nearly transparent. A fish that is of particular use with the disclosed constructs and methods is the Albino Barb. Barb skin color is determined by pigment cells in the skin, which contain pigment granules called melanosomes. The number, size, and density of the melanosomes per pigment cell influence the color of the fish skin. Albino Barb have diminished number, size, and density of melanosomes and hence have lighter skin when compared to the wild type barb.

Fertilization from Frozen Sperm

Fish sperm freezing methods are well-known in the art; see, e.g., Walker and Streisinger (1983) and Draper and Moens (2007), both of which are incorporated herein by reference in their entireties. To obtain the transgenic fish disclosed herein, frozen barb sperm may be used to fertilize eggs Briefly, one or two breeding pairs of barb should be placed in a shoebox with an artificial spawning mat. The water level in the shoebox should be ~2-3 inches and kept at 75-85° F. Low salinity (conductivity 100-200 uS/cm) and slight acidity (~pH 6.9) promote spawning. The fish may be exposed to a natural or artificial light cycle; the photoperiod starts at 8 am and ends at 10 pm. The following morning, remove and discard the eggs. Barb may be anesthetized by immersion in tricaine solution at 16 mg/100 mL water. After gill movement has slowed, remove one female, rinse it in water, and gently blot the belly damp-dry with a paper towel. The eggs should not be exposed to water as this will prevent fertilization. Gently squeeze out the eggs onto a slightly concave surface by applying light pressure to the sides of the abdomen with a thumb and index finger and sliding the fingers to the genital pore. Ready to spawn females will release the eggs extremely easily, and care should be taken not to squeeze the eggs out while blotting the fish. Good eggs are yellowish and translucent; eggs that have remained in the female too long appear white and opaque. The females will release the eggs only for an hour or so. Eggs from several females may be pooled; the eggs can be kept unfertilized for several minutes. The sperm is thawed at 33° C. in a water bath for 18-20 seconds. 70 µl room temperature Hanks solution is added to the vial and mixed. The sperm is then immediately added to the eggs and gently mixed. The sperm and eggs are activated by adding 750 µl of fish water and mixing. The mixture is incubated for 5 minutes at room temperature. The dish is then filled with fish water and incubated at 28° C. After 2-3 hours, fertile embryos are transferred to small dishes where they are further cultured.

Parichy and Johnson, 2001, which is incorporated by reference in its entirety, provides additional examples regarding in vitro fertilization.

The invention further encompasses progeny of a transgenic fish containing the Red barb 1 transformation event, as well as such transgenic fish derived from a transgenic fish egg, sperm cell, embryo, or other cell containing a genomically integrated transgenic construct. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The hybrid progeny of these matings have the benefits of the transgene for fluorescence combined with the benefits derived from these other lineages.

The simplest way to identify fish containing the Red barb 1 transformation event is by visual inspection, as the fish in question would be red colored and immediately distinguishable from non-transgenic fish.

EXAMPLES

Certain embodiments of the invention are further described with reference to the following examples. These examples are intended to be merely illustrative of the invention and are not intended to limit or restrict the scope of the present invention in any way and should not be construed as providing conditions, parameters, reagents, or starting materials that must be utilized exclusively in order to practice the art of the present invention.

Example 1

Red Transgenic Barb

Transgenic fish exhibiting a red color are provided. The specific transgenic events embodied in these fish are designated Red barb 1. Sperm from these fish may be used to fertilize barb eggs and thereby breed transgenic barb that comprise these specific transgenic integration events. On Dec. 19, 2016, 12 vials of Tiger Barb Sperm were submitted to the European Collection of Cell Cultures (ECACC). The submitted vials were labelled Barb 2016-R. The submission was given the Provisional Accession Number 16121901. The vials were submitted to the ECACC at the following address: ECACC, Culture Collections, Public Health England, Porton Down, Salisbury, SP4 0JG, UK.

The fluorescent transgenic fish have use as ornamental fish in the market. Stably expressing transgenic lines can be developed by breeding a transgenic individual with a wild-type fish, mutant fish, or another transgenic fish. The desired transgenic fish can be distinguished from non-transgenic fish by observing the fish in white light, sunlight, ultraviolet light, blue light, or any other useful lighting condition that allows visualization of the red color of the transgenic fish.

The fluorescent transgenic fish should also be valuable in the market for scientific research tools because they can be used for embryonic studies such as tracing cell lineage and cell migration. Additionally, these fish can be used to mark cells in genetic mosaic experiments and in fish cancer models.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

U.S. Pat. No. 7,135,613
U.S. Pat. No. 7,700,825
U.S. Pat. No. 7,834,239
Brem et al., *Aquaculture*, 68:209-219, 1988.
Chourrout et al., *Aquaculture*, 51:143-150, 1986.
Delvin et al., *Nature*, 371:209-210, 1994.
Draper and Moens, In: *The Zebrafish Book*, 5th Ed.; Eugene, University of Oregon Press, 2007.
Du et al., *Bio/Technology*, 10:176-181, 1992.
Innes, W. T., *Exotic Aquarium Fishes: A work of general reference*, Innes Publishing Company, Philadelphia, 1950.
Gross et al., *Aquaculature*, 103:253-273, 1992.
Khoo et al., *Aquaculture*, 107:1-19, 1992.
Lamason et al., *Science*, 310(5755):1782-1786, 2005.
Penman et al., *Aquaculture*, 85:35-50, 1990.
Powers et al., *Mol. Marine Biol. Biotechnol.*, 1:301-308, 1992.
Sin et al., *Aquaculture*, 117:57-69, 1993.
Szelei et al., *Transgenic Res.*, 3:116-119, 1994.
Tsai et al., *Can. J. Fish Aquat. Sci.*, 52:776-787, 1995.
Walker and Streisinger, *Genetics* 103: 125-136, 1983.
Xu et al., *DNA Cell Biol.*, 18, 85-95, 1999.
Zelenin et al., *FEBS Lett.*, 287(1-2):118-120, 1991.
Zhu et al., *Z. Angew. Ichthyol.*, 1:31-34, 1985.

What is claimed is:

1. A method of breeding barbs comprising:
   (a) obtaining a first transgenic barb that exhibits fluorescence and comprises a chromosomally integrated expression cassette encoding a fluorescent protein, the expression cassette comprised by the "Red barb 1 transformation event," sperm comprising the Red barb 1 transformation event having been deposited as ECACC accession no. 16121901, and
   (b) breeding the first transgenic barb with a second barb to obtain a third transgenic barb hybrid comprising the "Red barb 1 transformation event".

2. The method of claim 1, wherein the third transgenic barb exhibits fluorescence.

3. The method of claim 1, wherein the second barb is a transgenic barb that exhibits fluorescence and comprises a chromosomally integrated expression cassette encoding a fluorescent protein, the expression cassette comprised by the "Red barb 1 transformation event", sperm comprising the "Red barb 1 transformation event" having been deposited as ECACC accession no. 1612901.

4. The method of claim 3, wherein the second barb is heterozygous for the "Red barb 1 transformation event".

5. The method of claim 4, wherein the first barb is heterozygous for the "Red barb 1 transformation event".

6. The method of claim 4, wherein the first barb is homozygous for the "Red barb 1 transformation event".

7. The method of claim 3, wherein the second barb is homozygous for the "Red barb 1 transformation event".

8. The method of claim 7, wherein the first barb is heterozygous for the "Red barb 1 transformation event".

9. The method of claim 7, wherein the first barb is homozygous for the "Red barb 1 transformation event".

10. The method of claim 1, wherein the second barb is a non-transgenic barb.

11. The method of claim 1, wherein the first barb is heterozygous for the "Red barb 1 transformation event".

12. The method of claim 1, wherein the first barb is homozygous for the "Red barb 1 transformation event".

\* \* \* \* \*